United States Patent [19]

Kan et al.

[11] Patent Number: 5,071,966
[45] Date of Patent: Dec. 10, 1991

[54] PROCESS FOR PREPARING AN ENOL SILYL ETHER COMPOUND

[75] Inventors: Kazunori Kan, Kobe; Hiroshi Murakami; Nobuo Nagashima, both of Takasago; Noboru Ueyama, Kakogawa; Takehisa Ohashi, Kobe, all of Japan

[73] Assignee: Kanegafuchi Kagaku Kogyo Kabushiki Kaisha, Osaka, Japan

[21] Appl. No.: 576,499
[22] PCT Filed: Jan. 12, 1990
[86] PCT No.: PCT/JP90/00038
   § 371 Date: Sep. 10, 1990
   § 102(e) Date: Sep. 10, 1990
[87] PCT Pub. No.: WO90/08149
   PCT Pub. Date: Jul. 26, 1990

[30] Foreign Application Priority Data

Jan. 12, 1989 [JP] Japan ......................... 1-5800
Jun. 15, 1989 [JP] Japan ......................... 1-153099

[51] Int. Cl.$^5$ ........................................... C07C 113/00
[52] U.S. Cl. .................................................... 534/558
[58] Field of Search ......................................... 534/558

[56] References Cited

U.S. PATENT DOCUMENTS 4,525,582  6/1985  Amato et al. .................. 534/558
4,683,296  7/1987  Ueda et al. .................... 534/558

Primary Examiner—Paul F. Shaver
Attorney, Agent, or Firm—Armstrong, Nikaido, Marmelstein, Kubovcik & Murray

[57] ABSTRACT

A process for preparing an enol silyl ether compound from a diazoacetoacetic acid ester having the general formula (IV):

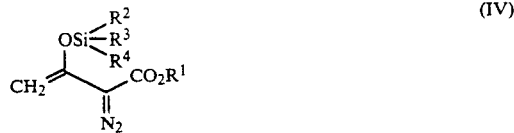

wherein $R^1$ is a lower alkyl group having 1 to 6 carbon atoms, phenyl group, a substituted phenyl group, an aralkyl group or allyl group, and $R^2$, $R^3$ and $R^4$ are the same or mutually different and each is a lower alkyl group having 1 to 6 carbon atoms, which comprises reacting a diazoacetoacetic acid ester having the general formula (I):

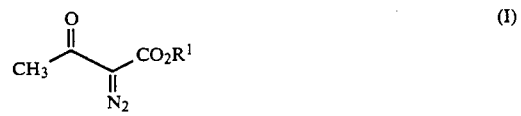

wherein $R^1$ is the same as defined above, with a trialkylsilyl chloride having the general formula (II):

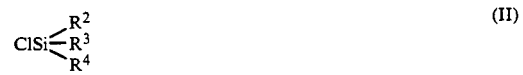

wherein $R^2$, $R^3$ and $R^4$ are the same as defined above, in an inert solvent in the presence of an organic base and an alkali halide having the general formula (III):

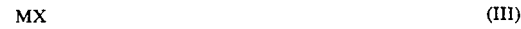

wherein M is an alkaline metal and X is bromine atom or iodine atom. The desired compound is useful as an intermediate for synthesis of carbapenem β-lactam antibiotics.

6 Claims, No Drawings

PROCESS FOR PREPARING AN ENOL SILYL ETHER COMPOUND

DESCRIPTION

1. Technical Field

The present invention relates to a process for preparing an enol silyl ether compound which is a useful intermediate for use in synthesis of carbapenem β-lactam antibiotics, typically thienamycin, known as β-lactam antibiotics of the fourth generation.

2. Background Art

Generally a diazo compound having the general formula (V):

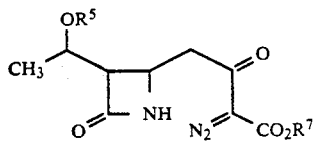

wherein $R^7$ is a protecting group for carboxyl group and $R^5$ is hydrogen atom or a protecting group for hydroxyl group, is well known as an intermediate for synthesis of the carbapenem β-lactam antibiotics. It is also known that the compound of the formula (V) is readily synthesized in a good yield by the synthetic method shown in the following reaction scheme:

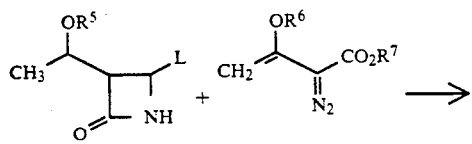

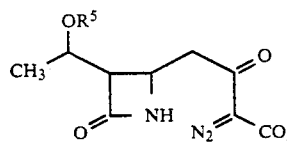

wherein $R^5$ and $R^7$ are the same as defined above, $R^6$ is a trialkylsilyl group, and L is a releasing group (cf., for example, Tetrahedron Letters, 23, 2293 (1982), Journal of the American Chemical Society, 103 (22), 6765 (1981), Japanese Unexamined Patent Publication No. 59-170096).

The present inventors earlier developed a simple method for preparing 4-acetoxy-3-hydroxyethylazetidin-2-one derivative used in the above-mentioned reaction (cf. Japanese Unexamined Patent Publication No. 61-18791 and No. 61-18758).

Accordingly, an enol silyl ether compound from a diazoacetoacetic acid ester, which is the desired compound of the present invention, is useful as an intermediate for synthesis of carbapenem β-lactam antibiotics.

Heretofore an enol silyl ether from a diazoacetoacetic acid ester was synthesized by using a triorganosilyl halide as a silylating agent in the presence of a strong base, e.g. lithium hexamethyldisilazide, according to the following reaction:

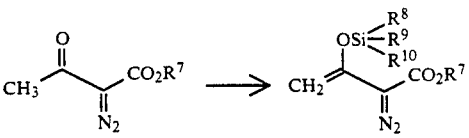

wherein $R^7$ is the same as defined above, and $R^8$, $R^9$ and $R^{10}$ are the same or mutually different and each is an alkyl group having 1 to 4 carbon atoms (cf. Japanese Unexamined Patent Publication No. 58-103358).

The above reaction has a drawback that in the case that $R^7$ is p-nitrobenzyl group, a strong base cannot be used.

It is reported that in the case that $R^7$ is p-nitrobenzyl group, a corresponding enol silyl ether can be synthesized when the reaction is carried out using a silylating agent such as triorganosilyl triflate in the presence of trialkylamine (cf. Japanese Unexamined Patent Publication No. 59-170096).

However, such a silylating agent as triorganosilyl triflate causes the following problem in addition to problems in handling when it is used in large quantities. An aqueous solution containing fluorine-containing compounds such as trifluoromethanesulfonic acid which is generated in washing after the reaction cannot be drained as a waste water as it is. Although the solution must be subjected to a suitable treatment, it is not easy to conduct such a treatment.

In view of the above situation, the present inventors made extensive researches to solve the problems mentioned above and it has been found that when a diazoacetoacetic acid ester is reacted with a trialkylsilyl chloride in the presence of an organic base and an alkali halide, the diazoacetoacetic ester can be readily converted in a high yield into an enol silyl ether thereof, which leads to the completion of the present invention.

DISCLOSURE OF THE INVENTION

The present invention provides a process for preparing an enol silyl ether compound from a diazoacetoacetic acid ester having the general formula (IV):

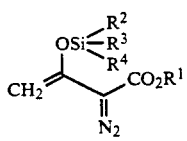

wherein $R^1$ is a lower alkyl group having 1 to 6 carbon atoms, phenyl group, a substituted phenyl group, an aralkyl group or allyl group, and $R^2$, $R^3$ and $R^4$ are the same or mutually different and each is a lower alkyl group having 1 to 6 carbon atoms, which comprises reacting a diazoacetoacetic acid ester having the general formula (I):

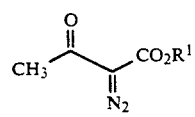

wherein $R^1$ is the same as defined above, with a trialkylsilyl chloride having the general formula (II):

(II)

wherein $R^2$, $R^3$ and $R^4$ are the same as defined above, in an inert solvent in the presence of an organic base and an alkali halide having the general formula (III):

MX  (III)

wherein M is an alkaline metal and X is bromine atom or iodine atom.

The diazoacetoacetic acid ester represented by the general formula (I) can be obtained by conventional methods. For example, ethyl acetoacetate is subjected to ester interchange with various alcohols, followed by diazotization, yielding various diazoacetoacetic acid esters.

With respect to the general formula (I), examples of the lower alkyl group having 1 to 6 carbon atoms represented by $R^1$ are methyl, ethyl, n-propyl and isopropyl. Examples of the substituted phenyl group represented by $R^1$ are methoxyphenyl and p-nitrophenyl. Examples of the aralkyl group represented by $R^1$ are p-nitrobenzyl and benzyl. Among the groups represented by $R^1$, p-nitrobenzyl and benzyl which are readily removed later are preferred and p-nitrobenzyl is especially preferred.

Examples of the trialkylsilyl chloride represented by the general formula (II) are trimethylsilyl chloride, tert-butyldimethylsilyl chloride, triethylsilyl chloride, triisopropylsilyl chloride, isobutyldimethylsilyl chloride, isopropyldimethylsilyl chloride, dimethyl-1,2-dimethylpropylsilyl chloride, and dimethyl-1,1,2-trimethylpropylsilyl chloride. In particular, trimethylsilyl chloride and tert-butyldimethylsilyl chloride are preferred.

Examples of the organic base are trialkylamines wherein the alkyl groups are the same or different and each is a lower alkyl group having 1 to 6 carbon atoms, including trimethylamine, triethylamine, tributylamine, tripropylamine and ethyldiisopropylamine. Triethylamine is especially preferred.

Examples of the alkali halide represented by the general formula (III) are sodium iodide, sodium bromide, lithium iodide, lithium bromide, potassium iodide and potassium bromide. Sodium iodide and lithium bromide are preferred and sodium iodide is especially preferred.

Examples of the inert solvent are acetonitrile, methylene chloride, chloroform, carbon tetrachloride, toluene, tetrahydrofuran and dimethylformamide. Acetonitrile is especially preferred.

The above-mentioned diazoacetoacetic acid esters, trialkylsilyl chlorides, organic bases, alkali halides and inert solvents may be used singly or in admixtures of two or more kinds thereof for each reagent.

According to the present invention, a trialkylsilyl chloride, which is a mild silylating agent, is converted into a more reactive silylating agent such as trialkylsilyl iodide or bromide by action of alkali halide in the reaction system. As a result, the enol silyl ether can be obtained without using any strong base or any specific silylating agent such as triorganosilyl triflate.

In the present invention, the trialkylsilyl chloride and the organic base are used in an amount of 1 equivalent or more, preferably 1 to 2 equivalents, respectively, per the diazoacetoacetic acid ester. The alkali halide is used in an amount of 1 equivalent or more, preferably 1 to 2 equivalents, per the diazoacetoacetic acid ester.

The order of addition of the components to the reaction system and other conditions are not particularly limited if the trialkylsilyl iodide or the like is formed under such conditions. Any procedure facilitating the operation under given conditions can be selected. An example is that a diazoacetoacetic acid ester, a trialkylsilyl chloride and an organic base are added to an inert solvent and then a solution of an alkali halide in an inert solvent is added thereto. Another example is that solid diazoacetoacetic acid ester such as the p-nitrobenzyl ester and an alkali halide are suspended or dissolved into an inert solvent and then an organic base and a trialkylsilyl chloride are added thereto. A further example is that a diazoacetoacetic acid ester, a trialkylsilyl chloride and an alkali halide are suspended or dissolved into an inert solvent and then an organic base is added thereto.

The reaction temperature can be selected from the range of $-10°$ C. to the boiling point of the solvent used. The degree of the progress of reaction can be followed by means of a neuclear magnetic resonance spectroscopy (NMR). In the case of obtaining an enol silyl ether unstable to water, a reaction mixture, after the reaction, is concentrated under a reduced pressure and a solvent such as hexane is added thereto. The resulting solution is filtered to remove insoluble materials and the solvent is distilled off under a reduced pressure to give a desired enol silyl ether. In the case of obtaining an enol silyl ether stable to water, a reaction mixture, after the reaction, is extracted with water and with an organic solvent such as methylene chloride or ethyl acetate. The organic layer is dried over a drying agent such as anhydrous sodium sulfate and then concentrated under a reduced pressure to give a desired enol silyl ether.

BEST MODE FOR CARRYING OUT THE INVENTION

The present invention will be explained by means of Examples and Application Examples.

EXAMPLE 1

[Synthesis of p-nitrobenzyl 2-diazo-3-trimethylsilyloxybutenoate]

To 1.5 ml of dry acetonitrile were added 100 mg (0.380 millimole) of p-nitrobenzyl 2-diazoacetoacetate, 64.8 μl (0.465 millimole) of triethylamine and 59 μl (0.465 millimole) of trimethylsilyl chloride. A solution obtained by dissolving 70 mg (0.467 millimole) of sodium iodide in 0.5 ml of dry acetonitrile was added dropwise thereto at a room temperature. After agitation for an hour, the reaction mixture was concentrated under a reduced pressure. After addition of 5 ml of hexane, insoluble materials were filtered off and the hexane was distilled off under a reduced pressure to give 115 mg (yield 90.1 %) of the desired compound in a yellow solid.

$^1$H NMR (90 MHz, CDCl$_3$)δ(ppm): 0.27 (9H, s), 4.22 (1H, d), 4.92 (1H, d), 5.31 (2H, s), 7.47 (2H, d), 8.22 (2H, d).

EXAMPLE 2

[Synthesis of p-nirobenzyl 2-diazo-3-tert-butyldimethylsilyloxybutenoate]

To 1.5 ml of dry acetonitrile were added 100 mg (0.380 millimole) of p-nitrobenzyl 2-diazoacetoacetate, 130 μl (0.933 millimole) of triethylamine and 140 mg (0.929 millimole) of tert-butyldimethylsilyl chloride. A solution obtained by dissolving 70 mg (0.467 millimole) of sodium iodide in 0.5 ml of dry acetonitrile was added dropwise thereto at a room temperature. After the conclusion of the dropwise addition, the reaction mixture was further agitated at 40° C. for 3 hours. To the reaction mixture was added 30 ml of methylene chloride, and the resultant was washed twice with 10 ml portions of water. The organic layer was dried over anhydrous sodium sulfate and concentrated under a reduced pressure to give 140 mg (yield 97.6 %) of the desired compound in a yellow solid.

$^1$H NMR (90 MHz, CDCl$_3$)δ(ppm): 0.27 (6H, s), 0.96 (9H, s), 4.25 (1H, d), 4.97 (1H, d), 5.32 (2H, s), 7.48 (2H, d), 8.22 (2H, d).

EXAMPLE 3

[Synthesis of benzyl 2-diazo-3-trimethylsilyloxybutenoate]

To 1.5 ml of dry acetonitrile were added 83 mg (0.380 millimole) of benzyl 2-diazoacetoacetate, 64.8 μl (0.465 millimole) of triethylamine and 59 μl (0.465 millimole) of trimethylsilyl chloride. A solution obtained by dissolving 70 mg (0.467 millimole) of sodium iodide in 0.5 ml of dry acetonitrile was added dropwise thereto at a room temperature. After agitation for an hour, the reaction mixture was concentrated under a reduced pressure. After addition of 5 ml of hexane, insoluble materials were filtered off and the hexane was distilled off under a reduced pressure to give 93 mg (yield 84.1 %) of the desired compound in a yellow solid.

$^1$H NMR (90 MHz, CDCl$_3$)δ(ppm): 0.28 (9H, s), 4.21 (1H, d), 5.00 (1H, d), 5.21 (2H, s), 7.31 (5H, s).

EXAMPLE 4

[Synthesis of benzyl 2-diazo-3-tert-butyldimethylsilyloxybutenoate]

To 1.5 ml of dry acetonitrile were added 83 mg (0.380 millimole) of benzyl 2-diazoacetoacetate, 130 μl (0.933 millimole) of triethylamine and 140 mg (0.929 millimole) of tert-butyldimethylsilyl chloride. A solution obtained by dissolving 70 mg (0.467 millimole) of sodium iodide in 0.5 ml of dry acetonitrile was added dropwise thereto at a room temperature. After the conclusion of the dropwise addition, the reaction mixture was further agitated at 40° C. for 4 hours. To the reaction mixture was added 30 ml of methylene chloride, and the resultant was washed twice with 10 ml portions of water. The organic layer was dried over anhydrous sodium sulfate and concentrated under a reduced pressure to give 118 mg (yield 93.7 %) of the desired compound in a yellow solid. $^1$H NMR (90 MHz, CDCl3) 4 (ppm): 0.28 (6H, s), 0.97 (9H, s), 4.24 (1H, d), 5.03 (1H, d), 5.21 (2H, s), 7.31 (5H, s).

EXAMPLE 5

[Synthesis of p-nitrobenzyl 2-diazo-3-trimethylsilyloxybutenoate]

Into 5 ml of dry acetonitrile were suspended 263 mg (1 millimole) of p-nitrobenzyl 2-diazoacetoacetate and 210 mg (1.4 millimoles) of sodium iodide. To the mixture were added 220 μl (1.6 millimoles) of triethylamine and then 190 μl (1.5 millimoles) of trimethylsilyl chloride while agitating in an argon atmosphere at a room temperature. After the resulting orange suspension was agitated at a room temperature for an hour, it was concentrated under a reduced pressure. To the residue was added 20 ml of dry hexane, and the resultant was agitated for 30 min. at a room temperature. Insoluble materials were removed by filtration and the hexane solution was concentrated to dryness under a reduced pressure to give 330 mg (yield 98 %) of the desired compound in a yellow solid. The physical properties of the product were in agreement with those of the product obtained in Example 1.

EXAMPLE 6

[Synthesis of p-nitrobenzyl 2-diazo-3-tert-butyldimethylsilyloxybutenoate]

Into 5 ml of dry acetonitrile were suspended 263 mg (1 millimole) of p-nitrobenzyl 2-diazoacetoacetate, 226 mg (1.5 millimoles) of tertbutyldimethylsilyl chloride and 210 mg (1.4 millimoles) of sodium iodide. To the mixture was added 220 μl (1.6 millimoles) of triethylamine under an argon atmosphere at a room temperature. The resultant was heated up to 40° C. and agitated at the same temperature overnight, followed by concentration under a reduced pressure. To the residue was added 20 ml of ethyl acetate, and the resultant was washed twice with 10 ml portions of water. The organic layer was dried and then concentrated to dryness under a reduced pressure to give 340 mg (yield 90%) of the desired compound in a yellow solid. The physical properties of the product were in agreement with those of the product obtained in Example 2.

EXAMPLE 7

[Synthesis of p-nitrobenzyl 2-diazo-3-isobutyldimethylsilyloxybutenoate]

Into 5 ml of dry acetonitrile were suspended 263 mg (1 millimole) of p-nitrobenzyl 2-diazoacetoacetate, 205 mg (1.5 millimoles) of isobutyldimethylsilyl chloride and 210 mg (1.4 millimoles) of sodium iodide. To the mixture was added 220 μl (1.6 millimoles) of triethylamine under an argon atmosphere at a room temperature. The resultant was heated up to 40° C. and agitated at the same temperature for 6 hours, followed by concentration under a reduced pressure. To the residue was added 20 ml of ethyl acetate, and the resultant was washed twice with 10 ml portions of water. The organic layer was dried and then concentrated to dryness under a reduced pressure to give 325 mg (yield 89%) of the desired compound in a yellow solid.

$^1$H NMR (90 MHz, CDCl$_3$)δ(ppm): 0.2 (6H, s), 0.97 (6H + 1H), 4.28 (1H, d, J=2 Hz), 4.98 (1H, d, J=2 Hz), 5.3 (2H, s), 7.5 (2H, d, J=8.4 Hz), 8.26 (2H, d, J=8.4 Hz).

EXAMPLE 8

[Synthesis of allyl 2-diazo-3-trimethylsilyloxybutenoate]

Into 5 ml of dry acetonitrile were added 167 mg (1 millimole) of allyl 2-diazoacetoacetate and 210 mg (1.4 millimoles) of sodium iodide. To the mixture were added 220 μl (1.6 millimoles) of triethylamine and then 190 μl (1.5 millimoles) of trimethylsilyl chloride while agitating under an argon atmosphere at a room temperature. After the resultant was agitated at a room temperature for an hour, it was concentrated under a reduced pressure. To the residue was added 10 ml of dry hexane, and the resultant was agitated for 30 min. at a room temperature. Isoluble materials were removed by filtration and the hexane solution was concentrated to dryness under a reduced pressure to give 176 mg (yield 78.8%) of the desired compound in an oily state.

$^1$H NMR (90 MHz, CDCl$_3$)δ(ppm): 0.21 (9H, s), 4.15 (1H, d, J=2 Hz), 4.63 (2H, d, J=5 Hz), 4.94 (1H, d, J=2 Hz), 5.0 to 6.3 (3H, m)

EXAMPLE 9

[Synthesis of p-nitrobenzyl 2-diazo-3-trimethylsilyloxybutenoate]

Into 5 ml of dry acetonitrile were suspended 263 mg (1 millimole) of p-nitrobenzyl 2-diazoacetoacetate and 122 mg (1.4 millimoles) of lithium bromide. To the mixture were added 220 μl (1.6 millimoles) of triethylamine and then 190 μl (1.5 millimoles) of trimethylsilyl chloride while agitating under an argon atmosphere at a room temperature. The resultant was heated up to 40° C. and agitated at the same temperature overnight, followed by concentration under a reduced pressure. To the residue was added 20 ml of dry hexane, and the resultant was agitated for 30 min. at a room temperature. Insoluble materials were removed by filtration and the filtrate was concentrated to dryness under a reduced pressure to give 330 mg (yield 87%) of the desired compound in a yellow solid. The physical properties of the product were in agreement with those of the product obtained in Example 1.

APPLICATION EXAMPLE 1

[Synthesis of (3S,4R)-3-[(1R)-tert-butyldimethylsilyl-oxyethyl]-4-[3-(p-nitrobenzyloxy)carbonyl-2-oxo-3-diazopropyl]azetidin-2-one]

A solution obtained by dissolving 403 mg (1.2 millimoles) of the above-mentioned p-nitrobenzyl 2-diazo-3-trimethylsilyloxybutenoate into 5 ml of dry acetonitrile was added to a mixture of 287 mg (1 millimole) of (3R,4R)-3-[(1R)-tert-butyldimethylsilyloxyethyl]-4-acetoxyazetizin-2-one and 80 mg (0.25 millimole) of anhydrous zinc iodide under an argon atmosphere at a room temperature. After continued agitation overnight, the reaction mixture was added to 20 ml of a saturated aqueous solution of sodium hydrogencarbonate with agitating. The resultant was extracted twice with 20 ml portions of ethyl acetate. After washing with water and drying, the organic layer was concentrated to dryness under a reduced pressure to give a yellow oily product. The oily product was subjected to a silica-gel column chromatography. The fractions which were eluted with hexane-acetone (4:1 by volume) were collected and concentrated under a reduced pressure to give 450 mg (yield 91.7%) of the desired compound in an oily state.

$^1$H NMR (90 MHz, CDCl$_3$)δ(ppm): 0.06 (6H, s), 0.83 (9H, s), 1.2 (3H, d, J=6.3 Hz), 2.8 to 3.5 (3H, m), 3.9 to 4.3 (2H, m), 5.33 (2H, s), 6.1 (1H, br.s), 7.53 (2H, d, J=8.8 Hz,) 8.25 (2H, d, J=8.8 Hz).

APPLICATION EXAMPLE 2

[Synthesis of (3S,4R)-3-[(1R)-tert-butyldimethylsilyl-oxyethyl]-4-[3-(p-nitrobenzyloxy)carbonyl-2-oxo-3-diazopropyl]azetidin-2-one]

A solution obtained by dissolving 453 mg (1.2 millimoles) of the above-mentioned p-nitrobenzyl 2-diazo3-tert-butyldimethylsilyloxybutenoate into 5 ml of dry acetonitrile was added to a mixture of 287 mg (1millimole) of (3R,4R)-3-[(1R)-tert-butyldimethylsilyloxyethyl]-4-acetoxyazetizin-2-one and 40 mg of (0.40 millimole) of anhydrous zinc chloride under an argon atmosphere at a room temperature. After continued agitation overnight, the reaction mixture was added to 20 ml of a saturated aqueous solution of sodium hydrogencarbonate with agitating. The resultant was extracted twice with 20 ml portions of ethyl acetate. After washing with water and drying, the organic layer was concentrated to dryness under a reduced pressure to give a yellow oily product. The crude product was treated in the same manner as in Application Example 1 to give 430 mg (yield 87.7%) of the desired compound. The physical properties of the compound was in agreement with those of the compound obtained in Application Example 1.

APPLICATION EXAMPLE 3

Synthesis of (3S,4R)-3-[(1R)-hydroxyethyl]-4-[3-(p-nitrobenzyloxy)-carbonyl-2-oxo-3-diazopro pyl]-azetidin-2-one]

Into 41 ml of dry acetonitrile were suspended 2.058 g (7.82 millimoles) of p-nitrobenzyl 2-diazoacetoacetate and 1.641 g (10.95 millimoles) of sodium iodide. To the suspension were added 1.74 ml (12.5 millimoles) of triethylamine and then 1.49 ml (11.73 millimoles) of trimethylsilyl chloride while agitating under an argon atmosphere at a room temperature. The resultant was agitated for an hour to give a suspension containing p-nitrobenzyl 2-diazo-3-trimethylsilyloxybutenoate.

The suspension was added to a mixture of 1.73 g (6.02 millimoles) of (3R,4R)-3-[(1R)-tert-butyldimethylsilyloxyethyl]-4-acetoxyazetizin-2-one and 770 mg (2.4 millimoles) of anhydrous sodium iodide and agitated at a room temperature overnight. The reaction mixture was added to 200 ml of a saturated aqueous solution of sodium hydrogencarbonate and agitated for 15 min. The aqueous layer was extracted twice with 100 ml portions of methylene chloride. After drying, the organic layer was concentrated under a reduced pressure to give a yellow oily product. The oily product was dissolved into 48 ml of methanol and 8.5 ml of 1N hydrochloric acid was added thereto, followed by agitation at a room temperature overnight. The resulting precipitate was taken by filtration and washed with cold methanol-water (9:1 by volume) and subsequently with hexane to give a white solid. The solid was recrystallized from acetone to give 1.84 g (total yield 81.2%) of the desired compound.

$^1$H NMR (90 MHz, CDCl$_3$)δ(ppm): 1.33 (3H, d, J=6.3 Hz), 2.6 (1H, br.s), 2.84 (1H, dd, J=7.3 Hz, 2.2 Hz), 3.25 (2H, m), 3.9 to 4.3 (2H, m), 5.36 (2H, s), 5.96 (1H, br.s), 7.53 (2H, d, J=8.6 Hz), 8.26 (2H, d, J=8.6 Hz).

As described above, in accordance with the present invention, an enol silyl ether compound from a diazoacetoacetic acid ester which is useful as an intermediate for synthesis of carbapenem β-lactam antibiotics is readily obtained in a high yield.

We claim:

1. A process for preparing an enol silyl ether compound from a diazoacetoacetic acid ester having the general formula (IV):

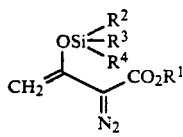 (IV)

wherein $R^1$ is a lower alkyl group having 1 to 6 carbon atoms, phenyl group, a substituted phenyl group, an aralkyl group or allyl group, and $R^2$, $R^3$ and $R^4$ are the same or mutually different and each is a lower alkyl group having 1 to 6 carbon atoms, which comprises reacting a diazoacetoacetic acid ester having the general formula (I):

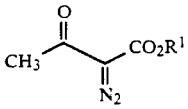 (I)

wherein $R^1$ is the same as defined above, with a trialkylsilyl chloride having the general formula (II):

 (II)

wherein $R^2$, $R^3$ and $R^4$ are the same as defined above, in an inert solvent in the presence of an organic base and an alkali halide having the general formula (III):

MX         (III)

wherein M is an alkaline metal and X is bromine atom or iodine atom.

2. The process of claim 1, wherein $R^1$ is p-nitrobenzyl group.

3. The process of claim 1, wherein said organic base is triethylamine.

4. The process of claim 1, wherein said inert solvent is acetonitrile.

5. The process of claim 1, wherein said trialkylsilyl chloride represented by the general formula (II) is trimethylsilyl chloride or tert-butyldimethylsilyl chloride.

6. The process of claim 1, wherein said alkali halide is sodium iodide.

* * * * *